(12) United States Patent
Fu et al.

(10) Patent No.: US 10,639,493 B2
(45) Date of Patent: May 5, 2020

(54) BLOOD MAGNETIC STIMULATION DEVICE

(71) Applicant: Venitas Research Center Inc., Mahe (SC)

(72) Inventors: Kun-Mei Fu, Taoyuan (TW); Con-Way Ho, La Palma, CA (US)

(73) Assignee: VENITAS RESEARCH CENTER INC., Mahé (SC)

( * ) Notice: Subject to any disclaimer, the term of this patent is extended or adjusted under 35 U.S.C. 154(b) by 285 days.

(21) Appl. No.: 15/873,785

(22) Filed: Jan. 17, 2018

(65) Prior Publication Data
US 2019/0217115 A1 Jul. 18, 2019

(51) Int. Cl.
| | |
|---|---|
| *A61N 1/00* | (2006.01) |
| *A61N 2/02* | (2006.01) |
| *A61M 1/36* | (2006.01) |
| *A61N 2/00* | (2006.01) |
| A61M 1/14 | (2006.01) |
| A61M 1/10 | (2006.01) |

(52) U.S. Cl.
CPC ............ *A61N 2/02* (2013.01); *A61M 1/3621* (2013.01); *A61N 2/004* (2013.01); *A61M 1/1001* (2014.02); *A61M 1/14* (2013.01)

(58) Field of Classification Search
CPC ........... A61N 2/02; A61N 2/004; A61M 1/36; A61M 1/1001; A61M 1/3621
USPC ....................................................... 600/9–15
See application file for complete search history.

(56) References Cited

U.S. PATENT DOCUMENTS

| | | | | |
|---|---|---|---|---|
| 5,131,904 | A * | 7/1992 | Markoll | ................... A61N 2/02 600/14 |
| 6,733,435 | B2 * | 5/2004 | Canedo | .................. A61N 2/008 600/9 |

* cited by examiner

*Primary Examiner* — John P Lacyk
(74) *Attorney, Agent, or Firm* — Sinorica, LLC

(57) ABSTRACT

A blood magnetic stimulation device includes a magnetic stimulation unit that has a stimulating coil for being connected to a blood delivering unit or directly worn by a user. The stimulating coil is further connected to a pulse-generating unit that outputs a pulse current to excite the stimulating coil, so as to use electromagnetic pulses to apply strong yet transient magnetic stimulation to blood passing through the magnetic stimulation unit or to blood in the user's subcutaneous vessels, thereby providing magnetic treatment for viremian and related diseases. As compared to the existing blood treating devices, the magnetic stimulation provided by the blood magnetic stimulation device incurs no sharp pain and uncomfortableness, and is safer and more acceptable to patients.

7 Claims, 5 Drawing Sheets

BLOOD MAGNETIC STIMULATION DEVICE

BACKGROUND OF THE INVENTION

1. Technical Field

The present invention relates to magnetic stimulation devices, and more particularly to a blood magnetic stimulation device that gives strong yet transient magnetic stimulation blood directly.

2. Description of Related Art

Throughout the literature on treatments of hematologic diseases, the most used solution is hemodialysis, which involves the use of osmosis membrane or hollow fiber membrane in hemodialysis machines to filter off metabolic wastes and impurities from blood, thereby purifying blood. However, the foregoing solution is only applicable to patients unable to expel toxic substances themselves, such as patients with chronic renal failure or blood poisoning, and is ineffective to patients with viremia or diseases related thereto, such as AIDS, viral encephalitis, viral hepatitis, trigeminal neuralgia, and herpes zoster.

In view of this, electrifying blood has been proposed as an alternative to eliminate viruses in blood. Nevertheless, direct electrification is dangerous and stimulation caused by electric currents can bring about sharp pain, making it less acceptable to patients. In a worst case, electrification can even destroy blood composition. For this reason, it has been only used in special cases in feasibility study, such as blood sterilization for blood donation. In view of this, the inventor of the present invention believes it is necessary to improve the existing hematologic diseases treating devices.

SUMMARY OF THE INVENTION

One objective of the present invention is to provide a magnetic stimulation device, which can directly give strong yet transient magnetic stimulation to blood so as to provide magnetic treatment against viremian and related diseases in the blood. As compared to the existing blood treating devices, the magnetic stimulation provided by the blood magnetic stimulation device incurs no sharp pain and uncomfortableness, and is safer and more acceptable to patients.

To achieve the forgoing objective, the present invention provides a magnetic stimulation device, which comprises: a magnetic stimulation unit, having a container that defines therein a chamber and is formed with an inlet and an outlet communicated with the chamber, and having a stimulating coil provided on the container to surround the chamber; a blood delivering unit, having an import pipe connected between a user's blood vessel and inlet of the container, and an export pipe connected between the outlet of the container and the user's blood vessel, thereby forming a blood track starting from the user's blood vessel, passing through the import pipe, the chamber of the container, and the export pipe successively, and returning to the user's blood vessel, and having a blood pump connected in series to the blood track for driving blood in the blood vessel to flow along the blood track; and a pulse-generating unit, being electrically connected to the stimulating coil for outputting a pulse current to excite the stimulating coil to generate a variational magnetic field, whereby, due to electromagnetic induction, an induced electric field is formed in the chamber, so that an induced current is generated to give strong yet transient magnetic stimulation to the blood passing through the chamber.

To achieve the forgoing objective, the present invention provides a magnetic stimulation device, which comprises: a magnetic stimulation unit, having a circular wearable that circles and defines therein an accommodating space with an inner surface thereof for accommodating a part of a user's body, and having a stimulating coil installed on the circular wearable for encircling the accommodating space; and a pulse-generating unit, being electrically connected to the stimulating coil for outputting a pulse current to excite the stimulating coil to generate a variational magnetic field, whereby, due to electromagnetic induction, an induced electric field is formed in the accommodating space, so that an induced current is generated in the user's subcutaneous vessels to give strong yet transient magnetic stimulation to the blood in the vessels.

The disclosed blood magnetic stimulation device uses the blood delivering unit to deliver the user's blood to the chamber of the container, and uses the pulse-generating unit to output the pulse current to excite the stimulating coil, thereby due to electromagnetic induction giving magnetic stimulation to blood passing through the chamber in order to provide magnetic treatment against all viremian and related diseases in the blood, such as AIDS, viral encephalitis, viral hepatitis, trigeminal neuralgia, herpes zoster and so on. In another embodiment, the circular wearable can be worn by a user, and then with the stimulating coil excited, a variational magnetic field is generate to directly generate an induced current in the user subcutaneous vessels, thereby allow noninvasive blood magnetic treatment based on electromagnetic pulses acting in the user's body. The magnetic stimulation usually lasts for a few milliseconds in each pulse, and the energy it carries is relatively limited. As compared to the existing blood treating devices, the magnetic stimulation provided by the blood magnetic stimulation device incurs no sharp pain and uncomfortableness, and is safer and more acceptable to patients.

DETAILED DESCRIPTION OF THE INVENTION

Figure 1:
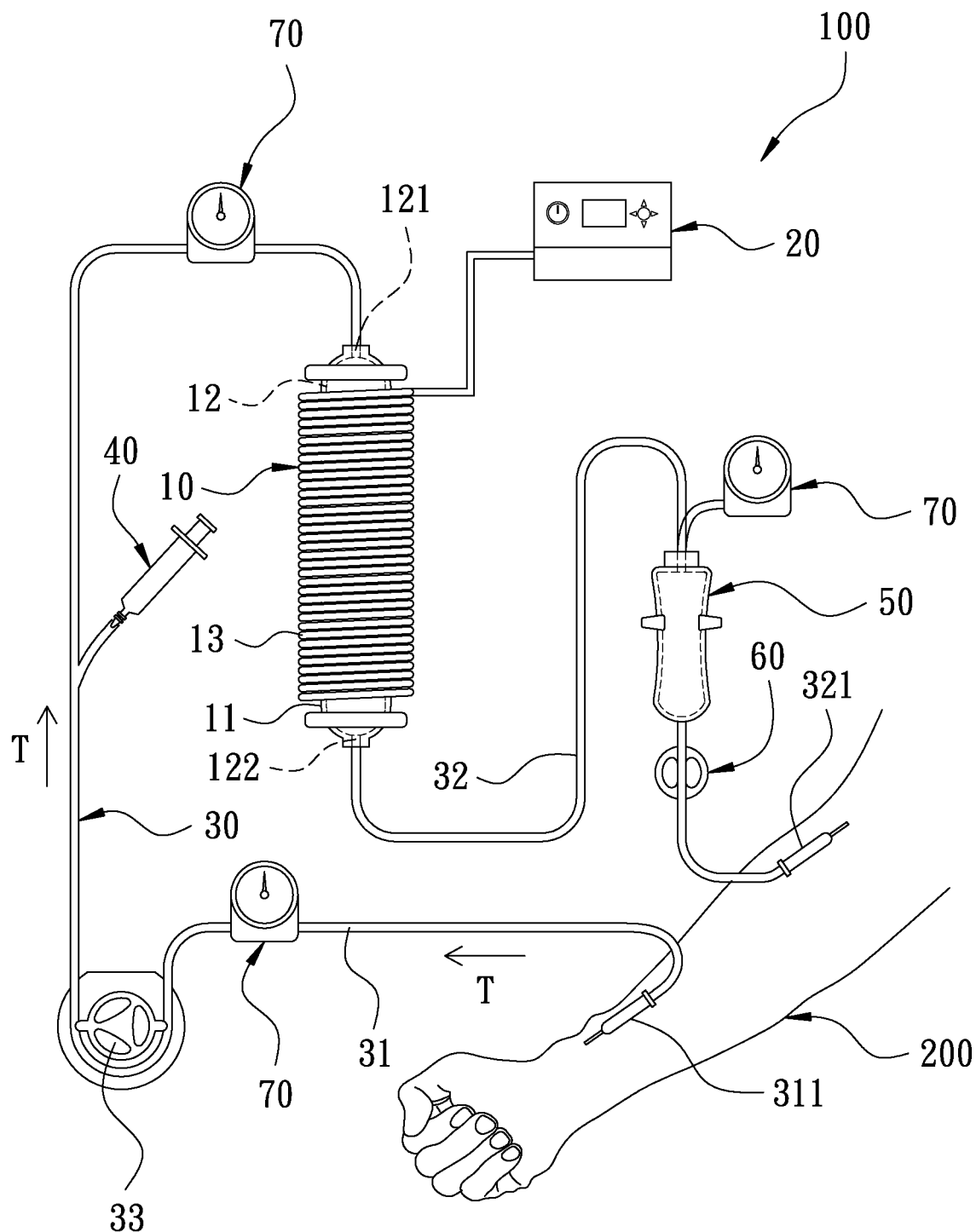
FIG. 1 is a schematic drawing showing the connection among components of a first preferred embodiment of the present invention.
Figure 2:
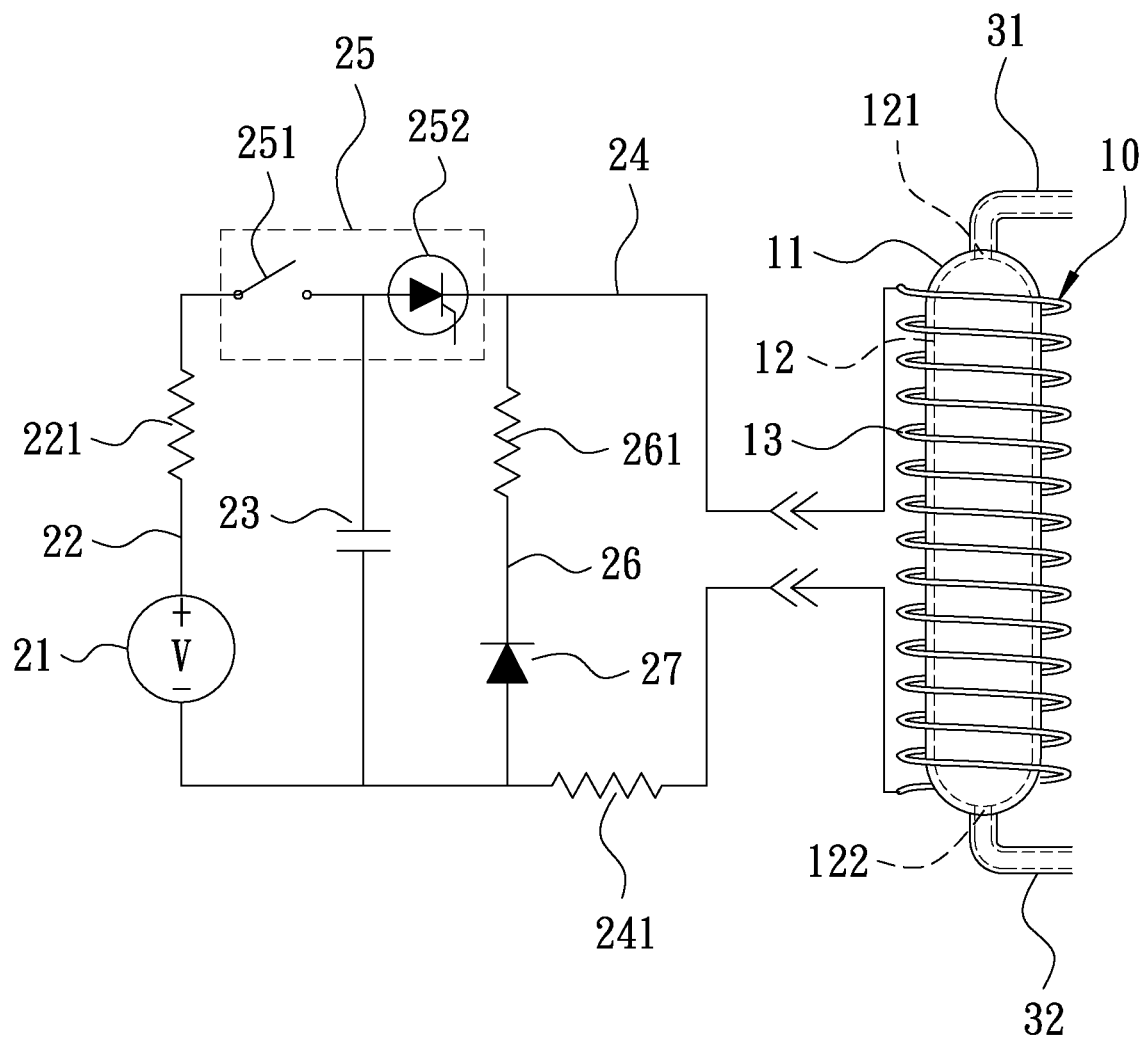
FIG. 2 is a circuit diagram of a pulse-generating unit in the first preferred embodiment of the present invention.

FIG. 1 and FIG. 2 are a schematic drawing showing the connection among components of a first preferred embodiment of the present invention and a circuit diagram of a pulse-generating unit in the first preferred embodiment of the present invention. As shown, a blood magnetic stimulation device 100 comprises: a magnetic stimulation unit 10, a pulse-generating unit 20, a blood delivering unit 30, an anticoagulation pump 40, a bubble monitor 50, a choke valve 60, and a plurality of pressure sensors 70.

The magnetic stimulation unit 10 has a container 11. The container 11 defines therein a chamber 12. The container 11 is provided with an inlet 121 and an outlet 122 at its outer surface that are communicated with the chamber 12. A stimulating coil 13 is wound around the container 11 to encircle the chamber 12. In the present embodiment, the container 11 is formed into a column-like shape, and preferably a cylindrical shape. The inlet 121 and the outlet 122 are formed at two ends of the container 11, respectively. The stimulating coil 13 is wound around the container 11 along the length of the container 11.

The pulse-generating unit 20 is electrically connected to the stimulating coil 13. Therein, as shown in FIG. 2, the pulse-generating unit 20 comprises a high-voltage DC source 21. The high-voltage DC source 21 is connected to a capacitor 23 through a charging circuit 22. The capacitor 23 is connected to the stimulating coil 13 through a discharging circuit 24. There is further a control module 25, which has a charging switch 251 located at the charging circuit 22, and a discharging switch 252 located at the discharging circuit 24. The discharging circuit 24 is connected to a branch circuit 26. The branch circuit 26 is provided with a pulse shaping module 27. The charging circuit 22 is provided with a current-limiting resistor 221, and the discharging circuit 24 is provided with a coil resistor 241, while the branch circuit 26 is provided with a branch resistor 261.

The blood delivering unit 30 has an import pipe 31 connected between a blood vessel of a user 200 and the inlet 121 of the container 11, and an export pipe 32 connected between the outlet 122 of the container 11 and the blood vessel of the user 200, thereby forming a blood track T starting from the blood vessel of the user 200, passing through the import pipe 31, the chamber 12 of the container 11, and the export pipe 32 successively, and returning to the blood vessel of the user 200. Therein, the import pipe 31 and the export pipe 32 are each connected to the vena of the user 200 through a fistula needle 331 or 332. In addition, a blood pump 33 is connected in series to the blood track T for driving blood in the blood vessel to flow along the blood track T.

The anticoagulation pump 40 is connected to the blood track T for injecting an antithrombotic drug.

The bubble monitor 50 is connected to the blood track T for monitoring whether there is any air bubble in the blood.

The choke valve 60 is connected to the blood track T for blocking the blood track.

The plural pressure sensors 70 are connected to the blood track T for monitoring the user's blood pressure at the blood track T.

Referring to FIG. 1 and FIG. 2, to use the blood magnetic stimulation device 100, the import pipe 31 and the export pipe 32 are first through the fistula needles 311, 321 connected to the blood vessel of the user 200, which is usually a vena. Then the blood pump 33 is activated to draw the blood in the blood vessel, and to drive the blood to flow along the blood track T. The blood thus flows into the chamber 12 at the inlet 121 through the import pipe 31, and then flows out the chamber 12 at the outlet 122, after which it flows along the export pipe 32 and returns to the blood vessel of the user 200. Meanwhile, the pulse-generating unit 20 is activated to make the control module 25 turn on the charging switch 251 and turn off the discharging switch 252 according to parameters set by the user. When the charging switch 251 is on, the high-voltage DC source 21 charges the capacitor 23. When the charging switch 251 is turned off and the discharging switch 252 is turned on, the capacitor 22 release the electricity it stores and outputs a pulse current to excite the stimulating coil 13 to generate a variational magnetic field. Thereby, due to electromagnetic induction, an induced electric field is formed in the chamber 12, so an induced current is generated to give strong yet transient magnetic stimulation to the blood passing through the chamber 12. In this way, magnetic treatment is provided against all possible viremian and related diseases in the blood, such as AIDS, viral encephalitis, viral hepatitis, trigeminal neuralgia, herpes zoster and so on. It is to be noted that viremia and other diseases recited herein are only illustrative, and not intended to limit the scope of the present invention.

Figure 3:
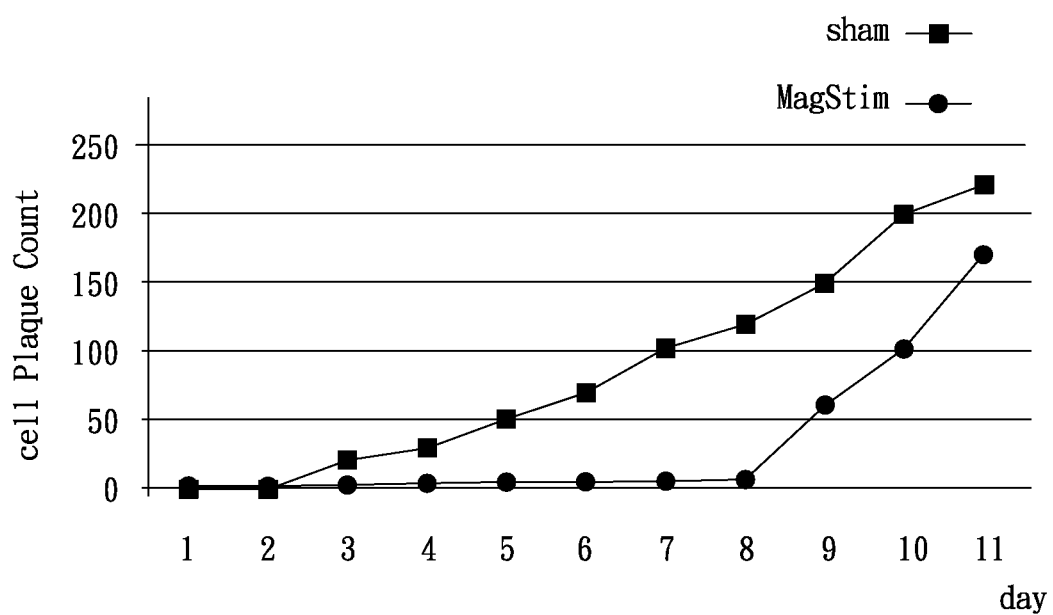
FIG. 3 is a plot graph showing experiment results of the first preferred embodiment of the present invention.

Now referring to FIG. 3, a plot graph showing experiment results of the first preferred embodiment of the present invention is shown. For verifying the effect of the disclosed device in the real world, we conducted an experiment where neuroblastoma was cultured. The numbers of cell plaques from the treated group (treated by magnetic stimulation) and from the control group (not treated by magnetic stimulation) were counted and recorded to get the data as shown in the graph of FIG. 3 where growth of herpes simplex virus can be observed. As shown, the count of cell plaques of the treated group was effectively controlled in the first 8 days, demonstrating that early proliferation of the virus can be inhibited by the magnetic treatment using magnetic stimulation.

Figure 4:
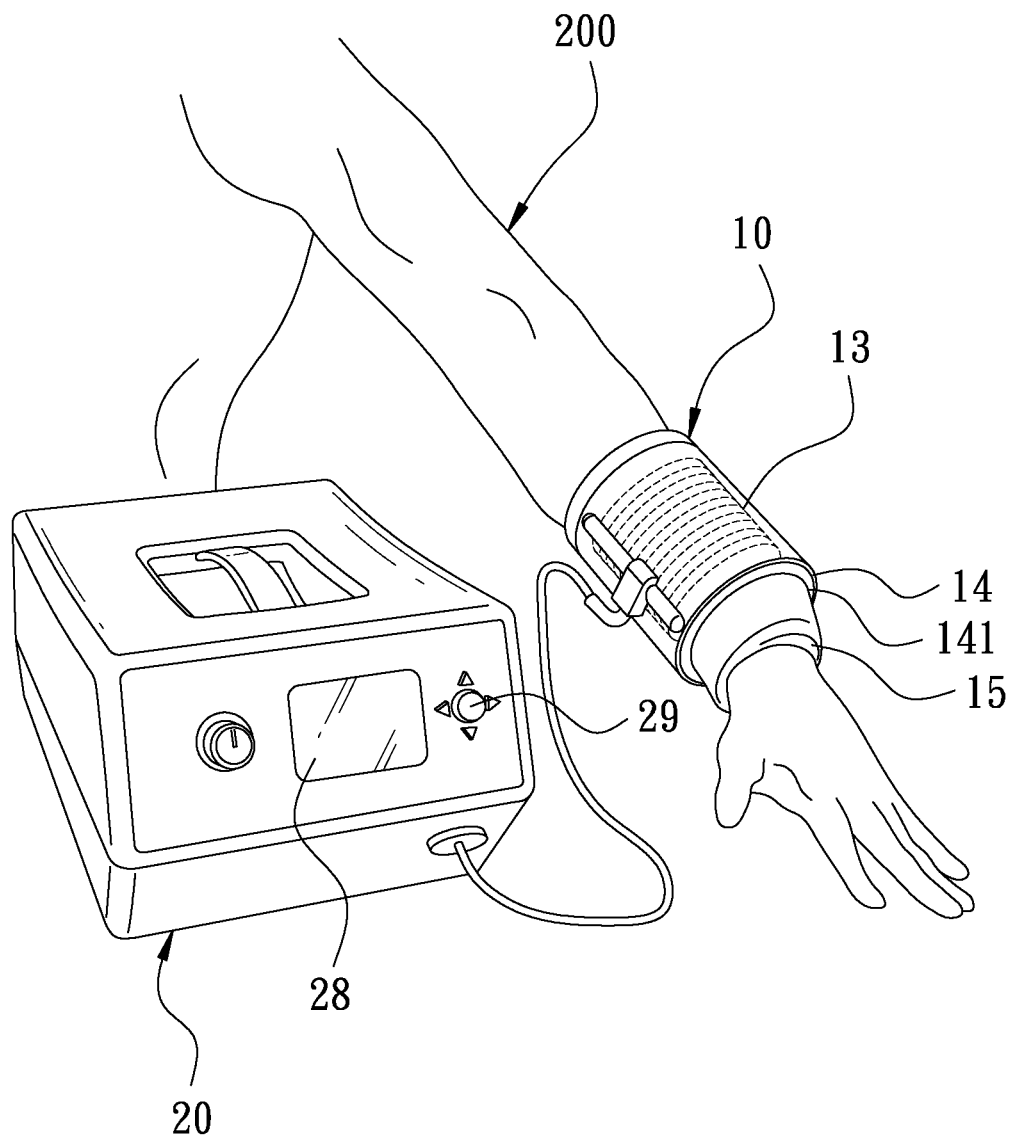
FIG. 4 is a schematic drawing showing the connection among components of a second preferred embodiment of the present invention.
Figure 5:
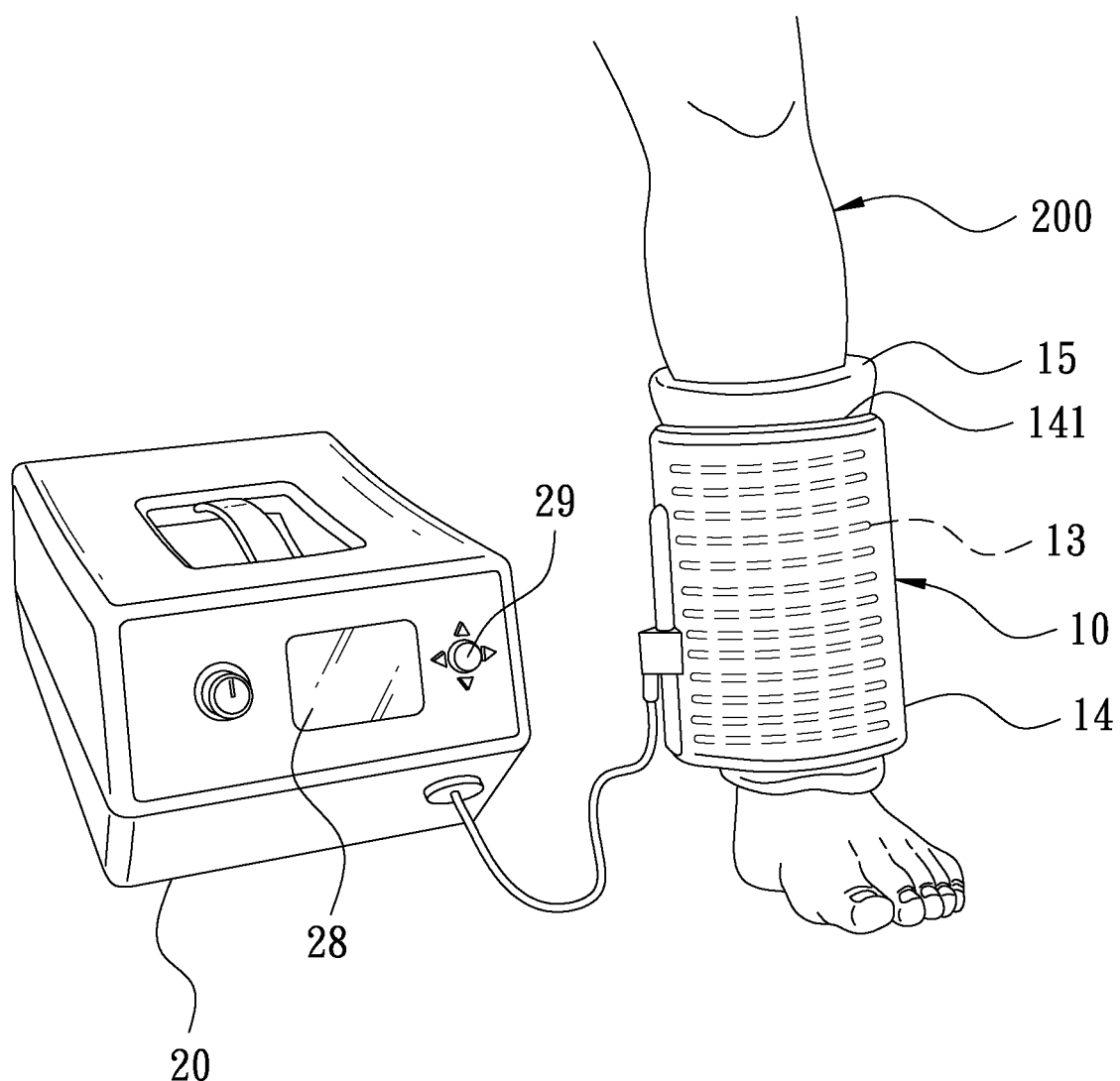
FIG. 5 is a schematic drawing showing the connection among components of a third preferred embodiment of the present invention.

FIG. 4 and FIG. 5 are schematic drawings showing the connection among components of second and third preferred embodiments of the present invention. They are different from the first preferred embodiment for that the magnetic stimulation unit 10 herein has a circular wearable 14, which circles and defines therein an accommodating space 141 for accommodating a part of the body of the user 200, such as the arm as shown in FIG. 4, or the leg as shown in FIG. 5. Additionally, the circular wearable 14 has the stimulating coil 13 installed thereon to encircle the accommodating space 141, and has a soft lining 15 annularly attached to the inner wall of the circular wearable 14 for making the magnetic stimulation unit 10 more comfortable to wear. The pulse-generating unit 20 is electrically connected to the stimulating coil 13 for outputting the pulse current to excite the stimulating coil 13 to generate a variational magnetic field. Thereby, due to electromagnetic induction, an induced electric field is formed in the accommodating space 141, so an induced current is generated to give strong yet transient magnetic stimulation to the blood passing through the user's subcutaneous vessels. In this way, as compared to the first preferred embodiment where the user's blood is drawn out of the body for receiving magnetic treatment, the second and third preferred embodiments allow noninvasive blood magnetic treatment based on electromagnetic pulses acting in the user's body.

It is to be noted that the pulse-generating unit 20 may further has a display module 28 and an operation module 29 for displaying and receiving the user's inputs of various parameters, which are used to program and control the charging/discharging frequency. Since the pulse-generating unit 20 is controlled by a switch, the entire circuitry can be held in a high-voltage DC environment. This not only helps to achieve the efficiency of the pulse-generating unit 20 above 80%, but also allow kilovolt-scale voltage to be output without using a transformer.

It is also to be noted that magnetic stimulation, as used herein, usually lasts for a few milliseconds in each pulse, and the energy it carries is relatively limited. As compared to the existing blood treating devices, the magnetic stimulation provided by the blood magnetic stimulation device incurs no sharp pain and uncomfortableness, and is safer and more acceptable to patients.

What is claimed is:

1. A blood magnetic stimulation device, comprising:
a magnetic stimulation unit, having a container that defines therein a chamber and is formed with an inlet and an outlet communicated with the chamber, and having a stimulating coil provided on the container to surround the chamber;
a blood delivering unit, having an import pipe connected between a user's blood vessel and inlet of the container, and an export pipe connected between the outlet of the container and the user's blood vessel, thereby forming a blood track starting from the user's blood vessel, passing through the import pipe, the chamber of the container, and the export pipe successively, and returning to the user's blood vessel, and having a blood pump connected in series to the blood track for driving blood in the blood vessel to flow along the blood track; and
a pulse-generating unit, being electrically connected to the stimulating coil for outputting a pulse current to excite the stimulating coil to generate a variational magnetic field, whereby, due to electromagnetic induction, an induced electric field is formed in the chamber, so that an induced current is generated to give strong yet transient magnetic stimulation to the blood passing through the chamber.

2. The blood magnetic stimulation device of claim 1, wherein the container is formed into a column-like shape, and the inlet and the outlet are provided at two ends of the container, while the stimulating coil is wound around and extend along a length of the container.

3. The blood magnetic stimulation device of claim 1, further comprising an anticoagulation pump that is connected to the blood track for injecting an antithrombotic drug.

4. The blood magnetic stimulation device of claim 1, further comprising a bubble monitor that is connected to the blood track for monitoring whether there is any air bubble in the blood.

5. The blood magnetic stimulation device of claim 1, further comprising a choke valve that is connected to the blood track for blocking the blood track.

6. The blood magnetic stimulation device of claim 1, further comprising a plurality of pressure sensors connected to the blood track for monitoring the user's blood pressure at the blood track.

7. The blood magnetic stimulation device of claim 1, wherein the pulse-generating unit comprises a high-voltage DC source connected to a capacitor through a charging circuit, and the capacitor is connected to the stimulating coil through a discharging circuit, the pulse-generating unit further comprising a control module that has a charging switch located at the charging circuit, and a discharging switch located at the discharging circuit, the discharging circuit being connected to a branch circuit, the branch circuit being provided with a pulse shaping module, the charging circuit being provided with a current-limiting resistor, and the discharging circuit being provided with a coil resistor, and the branch circuit being provided with a branch resistor.

* * * * *